United States Patent
Hudson et al.

(10) Patent No.: US 8,577,691 B2
(45) Date of Patent: Nov. 5, 2013

(54) PHARMACY SYSTEM DATA INTERFACE SYSTEM AND METHOD

(75) Inventors: Brian Marcus Hudson, Irving, TX (US); Matthew M. Bergmann, Franklin, TN (US); Barton K. Benson, Jr., Arlington, TX (US); William Rex Akers, Colleyville, TX (US); Travis John Bell, Garland, TX (US)

(73) Assignee: HCC, Inc., Fort Worth, TX (US)

( * ) Notice: Subject to any disclaimer, the term of this patent is extended or adjusted under 35 U.S.C. 154(b) by 2179 days.

(21) Appl. No.: 11/098,168

(22) Filed: Apr. 4, 2005

(65) Prior Publication Data
US 2006/0224415 A1 Oct. 5, 2006

(51) Int. Cl.
G06Q 10/00 (2012.01)
G06Q 50/00 (2012.01)
G06Q 40/00 (2012.01)
H04L 12/28 (2006.01)

(52) U.S. Cl.
USPC ............. 705/2; 705/3; 705/4; 370/351

(58) Field of Classification Search
USPC .......................... 705/2–4; 707/102
See application file for complete search history.

(56) References Cited

U.S. PATENT DOCUMENTS

| | | | |
|---|---|---|---|
| 5,704,044 A * | 12/1997 | Tarter et al. ............. | 705/4 |
| 5,911,132 A | 6/1999 | Sloane | |
| 6,343,271 B1 | 1/2002 | Peterson et al. | |
| 6,654,724 B1 | 11/2003 | Rubin et al. | |
| 6,687,676 B1 | 2/2004 | Denny | |
| 6,798,870 B1 * | 9/2004 | Lines et al. ............. | 379/100.09 |
| 2001/0037216 A1 | 11/2001 | Oscar et al. | |
| 2001/0047299 A1 | 11/2001 | Brewer et al. | |
| 2002/0002495 A1 * | 1/2002 | Ullman ............. | 705/21 |
| 2002/0077867 A1 | 6/2002 | Gittins et al. | |
| 2002/0107641 A1 | 8/2002 | Schaeffer et al. | |
| 2002/0165736 A1 | 11/2002 | Tolle et al. | |
| 2003/0055687 A1 | 3/2003 | Rudy | |
| 2003/0055809 A1 | 3/2003 | Bhat | |
| 2003/0149625 A1 | 8/2003 | Leonardi et al. | |
| 2003/0187615 A1 | 10/2003 | Epler et al. | |
| 2003/0236697 A1 | 12/2003 | Rupp | |
| 2004/0039599 A1 | 2/2004 | Fralic | |
| 2004/0054685 A1 * | 3/2004 | Rahn et al. ............. | 707/102 |

(Continued)

OTHER PUBLICATIONS

International Search Report of PCT/US2006/012425, Aug. 16, 2007, ISA/US.

(Continued)

Primary Examiner — Joseph Burgess
(74) Attorney, Agent, or Firm — Carr LLP (57) ABSTRACT

A method for receiving prescription data from a pharmacy is provided. The method includes emulating a device, such as using a pseudo TTY feature of a Unix operating system or a pseudo device of a Windows operating system. A prescription authorization system is then set to transmit data to the emulated device when the prescription data is provided to a claims approval agency by the prescription authorization system. The data can be supplemented with data from a secondary source, such as a system that acquires data in accordance with the Health Insurance Portability and Accountability Act or other suitable systems. The prescription data and any supplemental data is then received at the prescription authorization system, and is transmitted to the emulated device. The prescription data is also stored in a local log file, and is transmitted to a data warehouse over a network using the emulated device.

18 Claims, 7 Drawing Sheets

(56) References Cited

U.S. PATENT DOCUMENTS

| | | |
|---|---|---|
| 2004/0117323 A1 | 6/2004 | Mindala |
| 2004/0148195 A1 | 7/2004 | Kalies |
| 2004/0148196 A1 | 7/2004 | Kalies |
| 2004/0225528 A1 | 11/2004 | Brock |
| 2005/0065824 A1* | 3/2005 | Kohan .............................. 705/3 |
| 2005/0080651 A1* | 4/2005 | Morrison et al. ................. 705/2 |

OTHER PUBLICATIONS

Sage, Richard; Affidavit with Exhibits, Jul. 25, 2007.
U.S. Appl. No. 10/371,593; Office Action; Sep. 8, 2005.
U.S. Appl. No. 10/371,593; Response; Jan. 9, 2006.
U.S. Appl. No. 10/371,593; Office Action, Final; Jun. 1, 2006.
U.S. Appl. No. 10/371,593; Response; Nov. 1, 2006.
U.S. Appl. No. 10/371,593; Advisory Action; Nov. 28, 2006.
U.S. Appl. No. 10/371,593; Office Action; Mar. 9, 2007.
U.S. Appl. No. 10/371,593; Response; Aug. 9, 2007.
U.S. Appl. No. 10/371,593; Office Action, Restriction Requirement; Dec. 13, 2007.
U.S. Appl. No. 10/371,593; Response, Election; Jan. 14, 2008.
U.S. Appl. No. 10/371,593; Office Action, Final; Apr. 30, 2008.
U.S. Appl. No. 10/371,593; Response; Oct. 30, 2008.
U.S. Appl. No. 10/371,593; Office Action; Dec. 31, 2008.
U.S. Appl. No. 10/371,593; Office Action, Supplemental; Jun. 10, 2009.
U.S. Appl. No. 10/371,593; Response; Nov. 10, 2009.
U.S. Appl. No. 10/371,593; Office Action, Final; Jan. 21, 2010.
U.S. Appl. No. 10/371,593; Response; Jun. 21, 2010.
U.S. Appl. No. 10/371,593; Notice of Allowance; Sep. 30, 2010.
U.S. Appl. No. 10/371,593; Applicant's Interview Summary; Oct. 11, 2010.
U.S. Appl. No. 13/036,691; Office Action; Apr. 1, 2011.

* cited by examiner

PHARMACY SYSTEM DATA INTERFACE SYSTEM AND METHOD

FIELD OF THE INVENTION

The present invention pertains to the field of pharmacy systems, and more particularly to a system and method for obtaining data from a third party pharmacy system that does not require modification to the pharmacy system.

BACKGROUND OF THE INVENTION

Systems and methods for processing pharmacy data are known in the art. Most of these systems and methods are used to obtain authorization of charges for pharmaceutical prescriptions, such as by contacting a claims approval agency to determine whether a patient has insurance and what the patient should be charged in accordance with the patient's insurance policy. In particular, these systems can be designed to generate prescription data and prescription authorization data in compliance with National Council for Prescription Drug Programs (NCPDP) standards, such as the Telecommunication Standard Specification Version 5 Release 1 dated Sep. 1999, the Telecommunication Standard Implementation Guide Version 5 Release 1 dated Jun. 2000, the Data Dictionary dated September 1999, or other NCPDP standards, each of which are hereby incorporated by reference for all purposes.

While such systems and methods are useful, there are a large number of proprietary systems that are not readily integrated. Thus, in order to obtain information about the types of pharmaceutical compounds that are being dispensed by a large number of pharmacies, it would be necessary to develop and implement interfaces with a large number of proprietary systems.

SUMMARY OF THE INVENTION

In accordance with the present invention, a pharmacy system data interface system and method are provided that overcome known problems with obtaining data from multiple proprietary pharmacy systems.

In particular, a pharmacy system data interface system and method are provided that utilize existing proprietary systems as well as features of operating systems and communications systems to obtain data at a centralized location from multiple proprietary pharmacy systems, without requiring any modification to such proprietary pharmacy systems.

In accordance with an exemplary embodiment of the present invention, a method for receiving prescription data from a pharmacy is provided. The method includes emulating a device, such as using a pseudo TTY feature of a Unix operating system or a pseudo device of a Windows operating system. A prescription authorization system is then set to transmit data to the emulated device when the prescription data is provided to a claims approval agency by the prescription authorization system. The prescription data is then received at the prescription authorization system, and is transmitted to the emulated device. The prescription data is also stored in a local log file, and is transmitted to a data warehouse over a network using the emulated device.

The present invention provides many important technical advantages. In one important technical advantage of the present invention is a pharmacy system data interface system and method that can be used independently of the pharmacy system, such that prescription data from different pharmacy systems can be received and stored in a central location.

Those skilled in the art will further appreciate the advantages and superior features of the invention together with other important aspects thereof on reading the detailed description that follows in conjunction with the drawings.

DETAILED DESCRIPTION OF PREFERRED EMBODIMENTS

In the description that follows, like parts are marked throughout the specification and drawings with the same reference numerals, respectively. The drawing figures might not be to scale, and certain components can be shown in generalized or schematic form and identified by commercial designations in the interest of clarity and conciseness.

Figure 1:
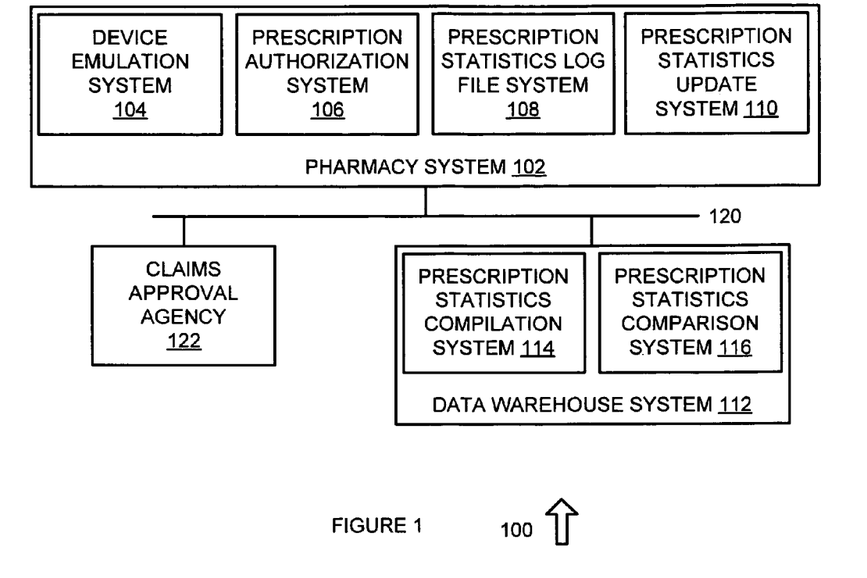
FIG. 1 is a diagram of a system for receiving prescription data from a pharmacy in accordance with an exemplary embodiment of the invention.

FIG. 1 is a diagram of a system 100 for receiving prescription data from a pharmacy in accordance with an exemplary embodiment of the invention. System 100 allows prescription data to be received from a prescription authorization software application even where the prescription authorization software application is not configured to transmit the prescription data to a third party source.

System 100 includes pharmacy system 102, which can be implemented in hardware, software, or a suitable combination of hardware and software, and which can be one or more software systems operating on a general purpose processing platform. As used herein, a software system can include one or more objects, agents, threads, lines of code, subroutines, separate software applications, two or more lines of code or other suitable software structures operating in two or more software applications or on two or more processors, or other suitable software structures. In one exemplary embodiment, a software system can include one or more lines of code or other suitable software structures operating in a general purpose software application, such as an operating system, and one or more lines of code or other suitable software structures operating in a specific purpose software application.

Pharmacy system 102 is coupled to data warehouse system 112 over communications medium 120, which can be a local area network, a wide area network, the Internet, the public switched telephone network; a wireless network, other suitable media, or a suitable combination of such media. As used herein, the term "coupled", and its cognate terms such as "couples" and "coupled", can include a physical connection (such as through a copper conductor), a virtual connection (such as through one or more randomly assigned memory locations in a data memory device), a logical connection (such as through one or more logical devices of a semiconducting circuit), a wireless connection, other suitable connections, or a suitable combination of such connections. In one exemplary embodiment, systems and components are coupled to other systems and components through intervening systems and components, such as through an operating system of a general purpose server platform.

Pharmacy system 102 includes device emulation system 104, prescription authorization system 106, prescription statistics log file system 108, and prescription statistics update system 110, each of which can be implemented in hardware, software, or a suitable combination of hardware and software, and which can be one or more software systems operating on a general purpose processing platform. Device emulation system 104 is used to emulate a device, such as a pseudo-TTY device, a pseudo device, or other suitable programs that operate in conjunction with Unix, Windows, or other operating systems that emulate the function of a device. Device emulation system 104 is configured to interface with prescription authorization system 106, such as by emulating a device that is operable to communicate with prescription authorization system 106.

Prescription authorization system 106 receives prescription data and obtains prescription authorization data from a third party claims approval agency. For example, when a customer presents a prescription to a pharmacy for filling, the pharmacy often requests insurance information from the customer and uses the insurance information to determine how much to charge the customer for the prescription, how much the insurance company for the customer will pay, and other information. Prescription authorization system 106 receives this data and interfaces with a claims approval agency 122 to obtain information to allow the pharmacy to charge the customer the correct amount.

Prescription statistics log file system 108 stores prescription statistics in a log file for subsequent use. In one exemplary embodiment, each time prescription authorization system 106 transmits prescription data to claims approval agency 122 or receives prescription authorization data from claims approval agency 122, that data can also be stored in prescription statistics log file system 108. Likewise, prescription statistics log file system 108 can provide other functions, such as to back up data for transmission to data warehouse system 112, for end of day reconciliation with data warehouse system 112, for providing delayed updates, for providing secondary source data or for other suitable purposes.

Prescription statistics update system 110 receives prescription data from device emulation system 104 and provides prescription statistics update data to prescription statistics log file system 108 and data warehouse system 112. In one exemplary embodiment, prescription statistics update system 110 interfaces with device emulation system 104, prescription authorization system 106, and prescription statistics log file system 108 to ensure that prescription statistics have been properly updated and that prescription statistics log file system 108 has been transmitted to data warehouse system 112 over device emulation system 104. For example, prescription statistics update system 110 can transmit data over an Internet connection or other suitable connections, whereas device emulation system 104 can emulate a modem or other device that would require a dial-up connection or other different types of unavailable physical connections.

Data warehouse system 112 includes prescription statistics compilation system 114 and prescription statistics comparison system 116, each of which can be implemented in hardware, software, or a suitable combination of hardware and software and which can be one or more software systems operating on a general purpose processing platform. Data warehouse system 112 can be operated in conjunction with claims approval agency 122, such as where data warehouse system 112 is a data switch having a contractual relationship with claims approval agency 122 to obtain prescription authorization data for a plurality of pharmacy systems 102. In another exemplary embodiment, prescription authorization system 106 can be a prescription authorization system that is configured for use with an external claims approval agency 122 and/or an associated switch that does not operate in conjunction with data warehouse system 112. In this exemplary embodiment, the other systems of pharmacy system 102 provide data to data warehouse system 112. Likewise, where prescription authorization system 106 is provided by an organization or claims approval agency 122 that is operating data warehouse system 112, then prescription authorization system 106 can also work in conjunction with the other systems of pharmacy system 102 or can directly transmit data to data warehouse system 112 as suitable.

Data warehouse system 112 receives prescription data and additional data to allow the prescription data to be used to determine prescription use information, prescription sales information, or other useful information regarding prescriptions. In one exemplary embodiment, data warehouse system 112 can be used to determine areas where marketing opportunities exist for selling equivalent pharmaceutical compounds, can be used to detect levels of pathogens that cause particular pharmaceutical compounds to be prescribed, such as to detect terrorist attacks using biological agents, to detect the spread of diseases in communities, or for other suitable purposes.

Prescription statistics compilation system 114 receives prescription data and compiles the prescription data in a database. In one exemplary embodiment, prescription statistics compilation system 114 can receive data as it is transmitted by prescription statistics update system 110. In another exemplary embodiment, prescription statistics compilation system 114 can receive bulk updates, such as when a data communications connection between the pharmacy system 102 and prescription statistics compilation system 114 has been unavailable but becomes available and a bulk update is transmitted for transactions that occurred when the data communications connection was unavailable. Likewise, prescription statistics compilation system 114 can store prescription data based on a record number, time of day received, pharmacy number, or other suitable data.

Prescription statistics comparison system 116 can receive an end of day file, a marker file, or other suitable file data and can determine whether a complete set of prescription data has been received from a pharmacy system 102. In one exemplary embodiment, prescription statistic comparison system 116 can receive data from pharmacy system 102 after a communications link has been interrupted or broken, such as prescription data that includes marker data indicating a sequence of prescription data transmission. In this exemplary embodiment, prescription statistics comparison system 116 can compare the last entry received from pharmacy system 102 and can ensure that duplicate entries are not entered into prescription statistics compilation system 114. Likewise, prescription statistics comparison system 116 can receive an end of day file from pharmacy system 102 and can compare entries in that file with entries stored in prescription statistics compilation system 114. In this exemplary embodiment, any discrepancies between the data in the end of day file and the data stored in prescription statistics compilation system 114 can be resolved, such as to eliminate duplicate entries, to add data that may not have been transmitted, and to identify situations where data has been received by prescription statistics compilation system 114 over the course of the day but where that data is not in the end of day file received from the pharmacy system 102. For example, a problem may exist where data is being transmitted to prescription statistics compilation system 114 from a secondary source that is not related to pharmacy system 102, or other suitable problems may exist that can also or alternatively be detected.

Claims approval agency 122 receives prescription data from prescription authorization system 106 and provides approval of the prescription data. In one exemplary embodiment, claims approval agency 122 can interface with insurance databases or agencies, can have a database of pre-approved personnel, or can have other information that can be used to determine both the eligibility for benefits and the cost to be charged for a prescription.

In operation, system 100 allows data to be received from a pharmacy system 102 at a data warehouse system 112, using a prescription authorization system 106 that is not operated by the operator of data warehouse system 112. System 100 allows prescription authorization system 106 to be configured so as to transmit data to a device emulation system 104, such that this data can be compiled in a prescription statistics log file system 108, and can be transmitted over an available communications medium to data warehouse system 112 by a prescription statistics update system 110.

Figure 2:
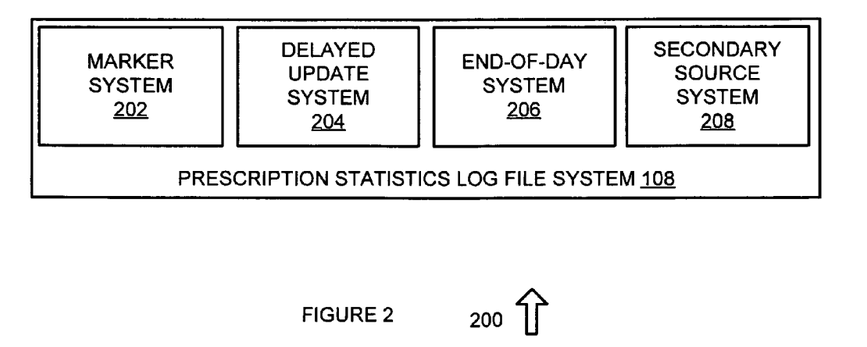
FIG. 2 is a diagram of a system for processing prescription data in accordance with an exemplary embodiment of present invention.

FIG. 2 is a diagram of a system 200 for processing prescription data in accordance with an exemplary embodiment of present invention. System 200 includes prescription statistics log file system 108 and marker system 202, delayed update system 204, end of day system 206, and secondary source system 208, each of which can be implemented in hardware, software or a suitable or combination of hardware and software, and which can be one or more software systems operating on a general purpose processing platform.

Marker system 202 generates marker data if transmission of prescription data to data warehouse system 112 is interrupted. In one exemplary embodiment, an Internet connection can be available for transmission of data to data warehouse system 112, a connection can be made with data warehouse system 112 by pharmacy system 102 using a periodic dial-up connection, or other suitable configurations can be used. Marker system 202 indicates in a data record where prescription data transmission has been interrupted, such as by indicating in a data record field that the data record has not been transmitted, or in other suitable manners.

Delayed update system 204 transmits prescription data to data warehouse system 112 that has been held due to unavailability of a communications medium. In one exemplary embodiment, delayed update system 204 can monitor for the availability or unavailability of a communications medium such as an Internet connection, and can also interface with marker system 202 to determine when prescription data has been stored and needs to be transmitted to a data warehouse system 112. Likewise, delayed update system 204 and marker system 202 can be used to store data when data is unavailable from other sources, such as secondary source system 208, prescription authorization system 106, or other suitable data.

End of day system 206 determines when an end of day has occurred, such as after a predetermined time when the pharmacy is no longer in operation for the day, at a predetermined time of the day that constitutes the end of the pharmacy's day of operation even when the pharmacy continues operating, or at other suitable times. End of day system 206 then transmits a log file that contains prescription data and additional data for the entire day period to data warehouse system 112. In this manner, data that has been stored in the log file for a pharmacy system 102 can be transmitted at the end of the day to confirm that a complete record of information has been received.

Secondary source system 208 contains additional data of interest to users of pharmaceutical data statistics, such as information regarding the patient, the physical location of the pharmacy, or other suitable data. In one exemplary embodiment, secondary source system 208 can be a system that is used to provide data in conformance with the Health Insurance Portability and Accountability Act, such as the name of a patient, the age of a patient, or other suitable data. Likewise, secondary source system 208 can remove such information where suitable, such as to comply with the Health Insurance Portability and Accountability Act or other suitable legislative requirements to protect privacy of individuals but to provide information regarding the number of units of a pharmaceutical compound that were dispensed, the date of delivery, patient physical data, or other suitable data.

In operation, system 200 allows a pharmacy system 102 to be used to compile prescription data for use by a data warehouse system 112, such as to allow the prescription data to be processed to detect trends in prescribing pharmaceuticals for treatments of diseases, to identify markets where pharmaceutical components are not used, to confirm the amount of pharmaceuticals in a market that are being consumed, such as to detect abuse or counterfeit pharmaceutical components, or other suitable data. System 200 thus allows marketing data, safety data, and other suitable data to be compiled.

Figure 3:
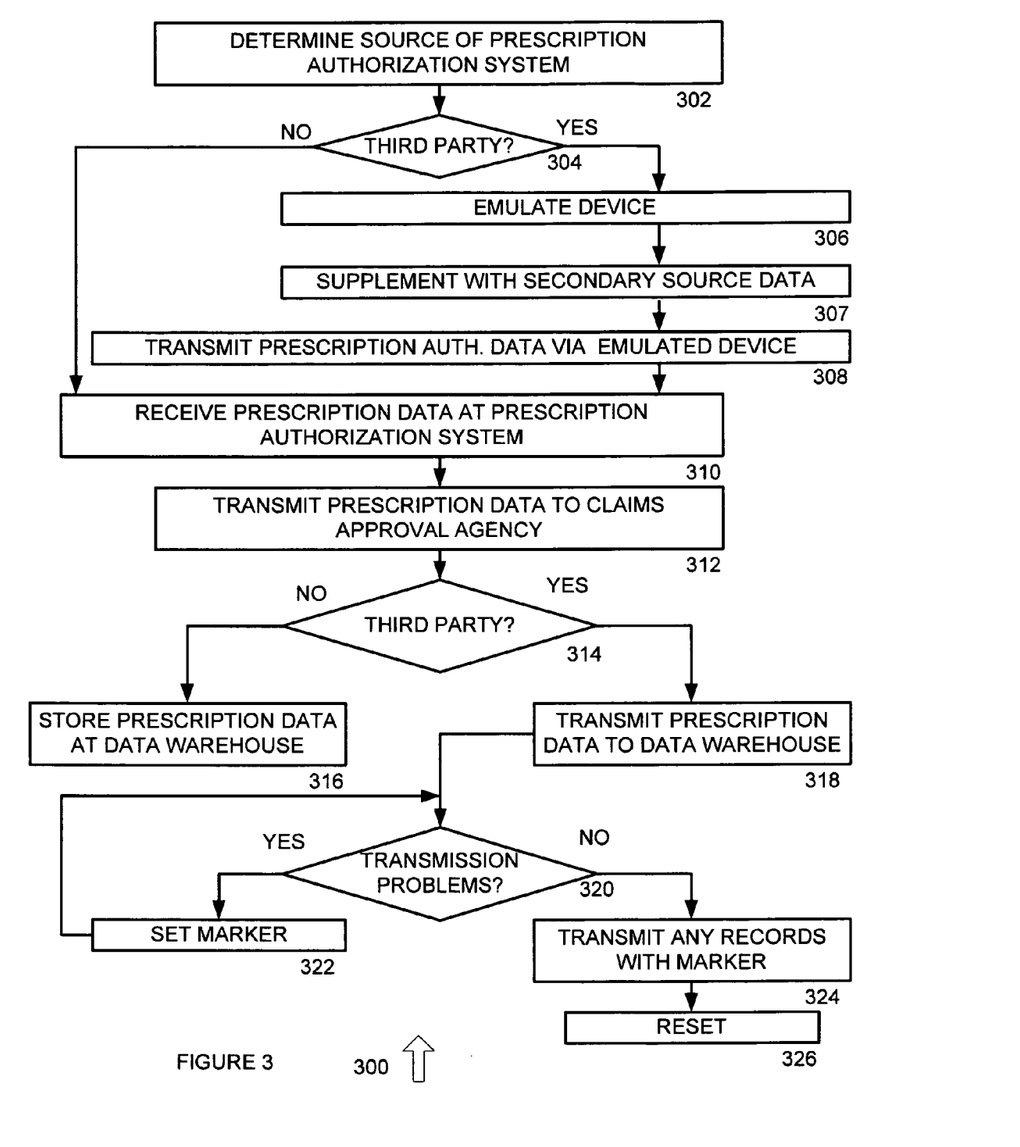
FIG. 3 is a flowchart of a method for transmitting prescription data to a data warehouse in accordance with an exemplary embodiment of the present invention.

FIG. 3 is a flowchart of a method 300 for transmitting prescription data to a data warehouse in accordance with an exemplary embodiment of the present invention. Method 300 allows data to be transmitted to a data warehouse system from a prescription authorization system, including one that is unaffiliated with the data warehouse system.

Method 300 begins at 302 where the source of the prescription authorization system is determined. For example, there may be many prescription authorization systems and operators, but obtaining non-confidential prescription use data from such sources at a central location can be difficult. If the prescription authorization system is not affiliated with an operator of a data warehouse, then it may be necessary to install additional systems in order to obtain such information. The method then proceeds to 304.

At 304 it is determined whether the source of the prescription authorization system is a third party. If the source is not a third party the method proceeds to 310. Otherwise, the method proceeds to 306 where a device is emulated. In one exemplary embodiment, the emulated device can be a device that the prescription authorization system is configured to interface with. The method then proceeds to 307.

At 307, the data is supplemented with secondary source data. In one exemplary embodiment, data from a system that is used to provide data in conformance with the Health Insurance Portability and Accountability Act or other suitable systems can be used to include the name of a patient, the age of a patient, or other suitable data. The method then proceeds to 308.

At 308 the prescription authorization system is set to transmit prescription authorization data to the emulated device. In one exemplary embodiment, the prescription authorization system can be configured to transmit data to a pseudo TTY, pseudo device, or other suitable alternate devices, can be configured to transmit to two or more communications channels in parallel, and can be configured in other suitable manners. After the prescription authorization system has been set to transmit to the emulated device the method proceeds to 310.

At 310 the prescription authorization data is received at a prescription authorization system. In one exemplary embodiment, the prescription authorization system can be a prescription authorization system that is operated in conjunction with a claims approval agency in order to determine a user's eligibility, the insurance company that is providing coverage to the user, the cost to the user for a prescription, the availability of alternates such as generics, other suitable data. The method then proceeds to 312.

At 312 the prescription data is transmitted to a claims approval agency. In one exemplary embodiment, the prescription data can be transmitted individually, such as in a single data packet or transmission message, it can be combined with other data, such as secondary source data and can be transmitted in parallel, such as to a first party (e.g. a prescription claims approval agency) and to a second party (e.g. a data warehouse), or it can be transmitted in other suitable manners. The method then proceeds to 314.

At 314 it is determined whether the claims approval agency and the data warehouse system are third parties or are otherwise unaffiliated. If it is determined that the claims approval agency is not a third party to the data warehouse system operator, the method proceeds to 316 where the prescription data is stored at the data warehouse. Otherwise, the method proceeds to 318 where the prescription data is transmitted to the data warehouse. As previously discussed, the prescription data that is transmitted to the data warehouse can include additional data that is obtained from a secondary source, such as data that allows prescription data to be associated with demographic information for the person who is receiving the prescription, while complying with privacy protection laws such as the Health Insurance Portability and Accountability Act or other suitable privacy laws. The method then proceeds to 320.

At 320 it is determined whether there are any transmission problems. For example, a communications link to the data warehouse, the claims approval agency or other suitable parties may be unavailable such that the data must subsequently be transmitted at a later time. In order to avoid loss of data or duplication of a prescription data log file, the method proceeds to 322 where a marker is set. In this manner, the prescription data can be marked as not having been transmitted such that when the communications channel is available for transmission, the untransmitted data alone can be transmitted to the data warehouse. The method then returns to 320 until it is determined that transmission problems have been resolved. The method then proceeds to 324.

At 324 any records with a marker are transmitted to the data warehouse. In one exemplary embodiment, if the pharmacy system 102 transmits prescription data to a claims approval agency 122, it can be determined whether such records match any records with markers or other suitable processes can be used. The method then proceeds to 326 where the transmission path is reset, such as to proceed with continuous transmission of prescription data to a data warehouse system 112.

In operation, method 300 allows prescription data to be transmitted to a data warehouse, regardless of whether the data warehouse is affiliated with a claims approval agency or not. Method 300 allows a device to be emulated that receives data to be transmitted to the data warehouse so as to allow a third party data warehouse system operator to receive prescription data. Likewise, method 300 allows a data warehouse that is affiliated with a claims approval agency, such as a pharmacy data switch organization, to receive the data without reconfiguring a prescription authorization system.

Figure 4:
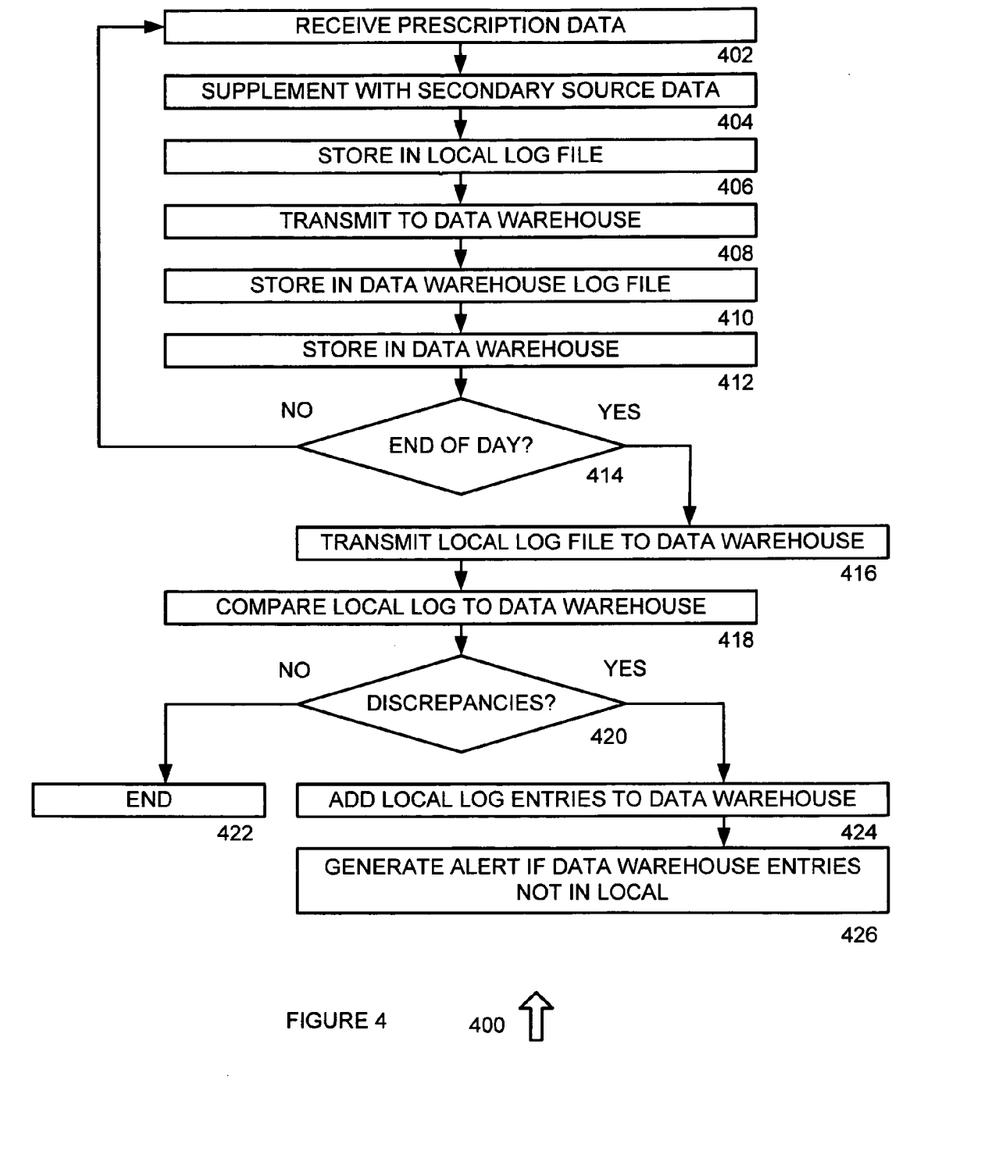
FIG. 4 is a flow chart of a method for ensuring the continuity of prescription data transmitted to a data warehouse in accordance with an exemplary embodiment of the present invention.

FIG. 4 is a flow chart of a method 400 for ensuring the continuity of prescription data transmitted to a data warehouse in accordance with an exemplary embodiment of the present invention. Method 400 begins at 402 where prescription data is received. In one exemplary embodiment, the prescription data can be received at a prescription authorization system 106 that interfaces with a claims approval agency for approval of the prescription data, approval of benefits and price data, confirmation of the prescription, or other suitable data. The method then proceeds to 404.

At 404 the prescription data is supplemented with secondary source data. The secondary source data can provide additional information regarding the patient that is receiving the prescription, such as information obtained from a system that is used to instruct the client of requirements under the Health Insurance Portability and Accountability Act, or other suitable systems. In this exemplary embodiment, a pharmacy system may obtain approval from patients to use their information for additional purposes, to use their information subject to certain restrictions regarding identification of the patient, or other suitable data. The method then proceeds to 406.

At 406 the prescription data supplemented with the secondary source data is stored in a local log file. In one exemplary embodiment, this log file can be maintained separately from the prescription authorization system 106, can be contained within prescription authorization system 106, or can be otherwise configured. The method then proceeds to 408.

At 408 the prescription data supplemented with the secondary source data is transmitted to a data warehouse. In one exemplary embodiment, transmission can occur when the prescription data is transmitted to the claims approval agency 122, such as when the claims approval agency 122 operates data warehouse system 112. Likewise, the transmission to the data warehouse can occur in parallel with transmission to a claims approval agency 122, can occur in multiple steps, such as with the prescription data being transmitted in a first data record or message and the secondary source data being transmitted in a second data record or message, or other suitable processes can be used. The method then proceeds to 410.

At 410 the data is stored in a data warehouse log file. In one exemplary embodiment, the data warehouse can contain a log file for each pharmacy that it receives data from, such as to allow daily correlation and confirmation of data that is transmitted to be performed. The method then proceeds to 412.

At 412 the pharmacy data, prescription data and additional second source data is stored in a data warehouse. In one exemplary embodiment, the data warehouse can store the information in a manner that allows it to be used for disease state management purposes, to determine areas of the country where infections are occurring, for homeland security, for the detection of biological agent attacks, for detection of the spread of infectious diseases, for marketing purposes, to determine areas of the country where certain pharmaceutical compounds are not being used or marketed, or for other suitable purposes. The method then proceeds to 414.

At 414 it is determined whether it is the end of the day. The end of the day can be an actual end of day when the pharmacy stops operations, can be an end of day when the pharmacy continues operating but completes its daily log transaction, or can be other suitable ends of day. If it is determined that it is not an end of day, the method returns to 402. Otherwise, the method proceeds to 416.

At 416 a local log file is transmitted to a data warehouse. In one exemplary embodiment, the local log file can store the pharmacy prescription data, the secondary source data, or other suitable data that has been logged over the course of the day. The method then proceeds to 418.

At 418 the local log file is compared to the data warehouse log file. In one exemplary embodiment, an exact comparison can be performed to determine whether each data record and entry matches the corresponding data record entry at the data warehouse. Likewise, record numbers can be compared or other suitable processes can be performed. The method then proceeds to 420.

At 420 it is determined whether any discrepancies exist in the data. If no discrepancies exist, the method then proceeds to 422 and ends. Otherwise, the method proceeds to 424 where local log entries that were present in the pharmacy data but which were not present in the data warehouse data are added to a data warehouse. Likewise, if it is determined that the local log entries may have been improperly added, such as if they lacked corresponding payment data or other suitable data that indicates that a pharmacy employee may have been stealing or otherwise misappropriating pharmaceuticals, alert data can be generated. The method then proceeds to 426.

At 426 alert data is generated if data warehouse entries are not in the local log file. In this situation, the data warehouse has received prescription data that appears to have been transmitted from a pharmacy at an earlier time, but which may have been received from a third party of other sources. Likewise, the pharmacy system, logging system, or other systems at the pharmacy may be misoperating such that data that is being transmitted to the data warehouse is not being stored in local log files. Likewise, this condition could be indicative of fraud or theft by pharmacy employees, or some other unwanted condition. In any event, additional information and investigation can be performed after receipt of the alert data to determine the source of the discrepancy.

In operation, method 400 allows prescription data to be matched with secondary data and to be transmitted to a data warehouse for use in disease state management, marketing analysis, or for other suitable purposes. Method 400 allows third parties that are not affiliated with a data switch or other system that provides access to a claims approval agency to receive prescription data and secondary source data that is associated with the prescription data.

Figure 5:
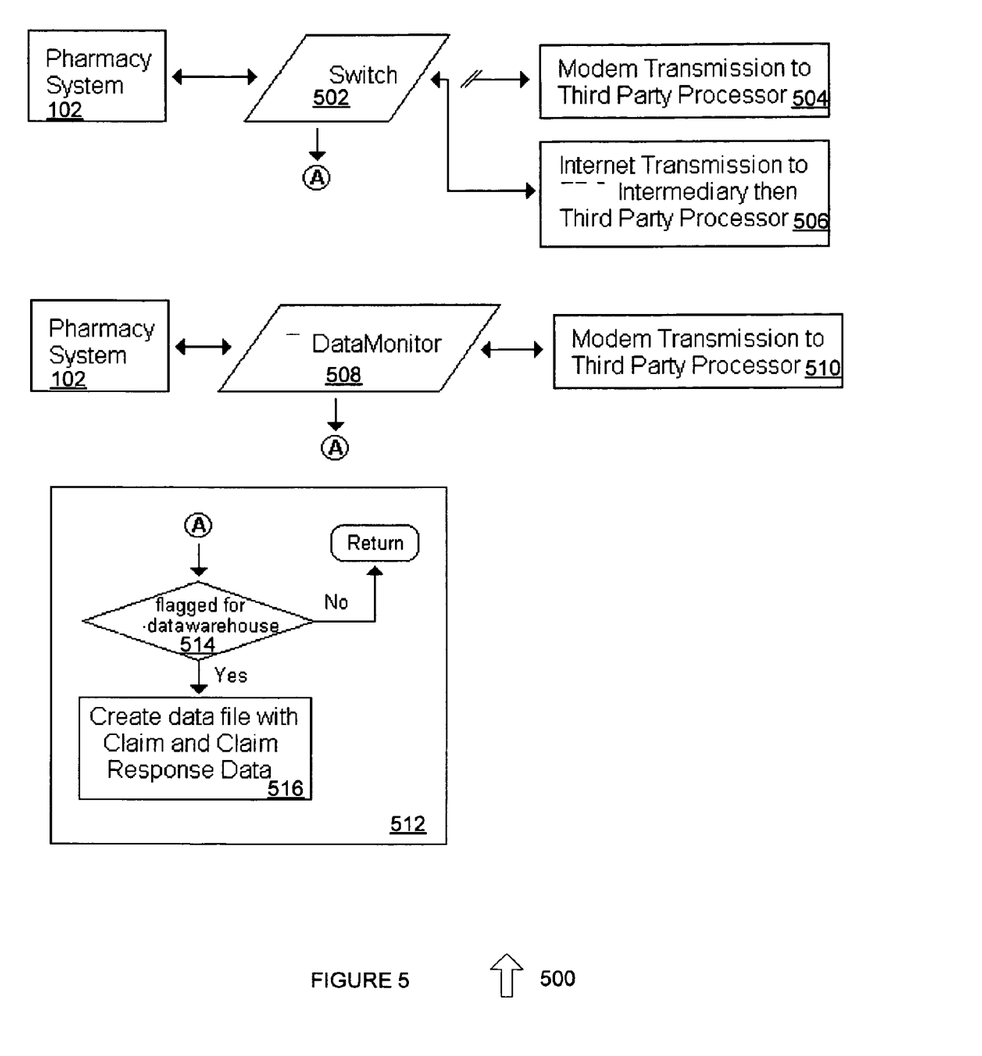
FIG. 5 is a diagram of a system for receiving prescription data in accordance with an exemplary embodiment of the present invention.

FIG. 5 is a diagram of a system 500 for receiving prescription data in accordance with an exemplary embodiment of the present invention. System 500 includes pharmacy system 102 which interfaces with local switch 502. Local switch 502 can be implemented in hardware, software, or a suitable combination of hardware and software, and can be one or more software systems operating on a general purpose processing platform. Local switch 502 monitors data from pharmacy system 102 for claim data and claim response data, transmits the claim data and the claim response data to a data warehouse, and stores data locally at the pharmacy for transmission at the end of day. In one exemplary embodiment, modem transmission of the claim data to a third party processor can occur at 504, and receipt of claim response data from the third party processor via the modem can be monitored by local switch 502. Likewise, transmission of the claim data over the Internet to an intermediary with a data warehouse and subsequent transmission of the claim data to a third party processor can be performed, as well as return of the claim response data from the third party processor through the intermediary.

In another exemplary embodiment, a data monitor 508 can be used at 510 to create an end-of-day data file prior to transmitting the claim data to a third party processor and after receiving the claim response data. Both processes can include determining at 514 whether a flag has been selected for the storing of claim data and claim response data for end-of-day transmission at 516, as well as for transmission to a data warehouse. In one exemplary embodiment, the end-of-day file can be used to transmit the claim data and the claim response data to the data warehouse if real-time updates are not available, such as over an Internet connection.

Figure 6:
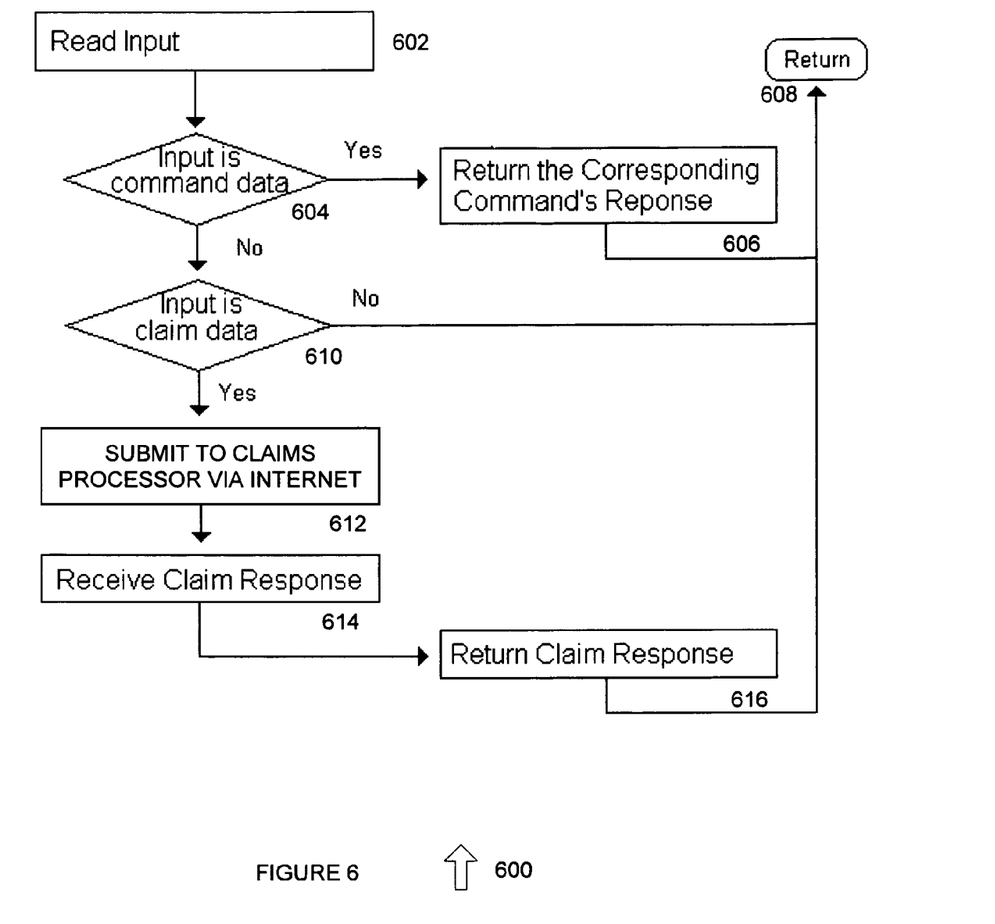
FIG. 6 is a flow chart of a method for determining whether to transmit prescription data to a switch from a pharmacy in accordance with an exemplary embodiment of the present invention.

FIG. 6 is a flow chart of a method 600 for determining whether to transmit prescription data to a switch from a pharmacy in accordance with an exemplary embodiment of the present invention. Method 600 begins at 602 where input data is read. If it is determined at 604 that the input data is command data, the method proceeds to 606 where the corresponding command response is generated, and the method returns at 608. Otherwise, the method proceeds to 610.

At 610 it is determined whether the input is claim data. If the input is not claim data, the method returns at 608. Otherwise, the method proceeds to 612 where the claim data is submitted for processing, such as via an Internet connection to a pharmacy switch system. The claim data can also be stored locally in a data file that is transmitted to the data warehouse or other suitable locations at the end of the day or at other suitable periods, can be stored in a data warehouse at the pharmacy switch system or in other suitable locations. The method then proceeds to 614.

At 614, claim response data is received. In one exemplary embodiment, the claim response data can be stored at a data warehouse prior to being transmitted, can be stored locally in a data file that is transmitted to the data warehouse or other suitable locations at the end of the day or at other suitable periods, or other suitable processes can be performed. The method then proceeds to 616 where the claim response is returned, and the method then returns at 608.

Figure 7:
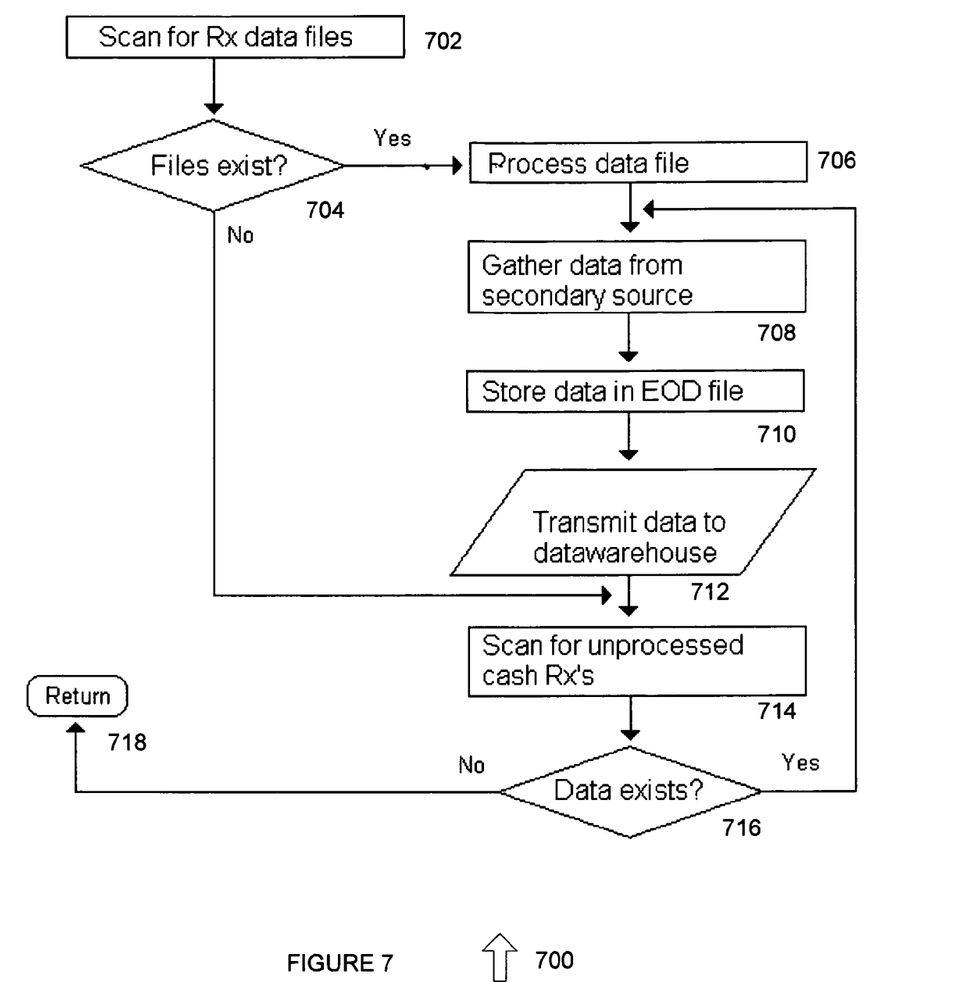
FIG. 7 is a flow chart of a method for determining whether to store prescription data for transmission to a switch from a pharmacy in accordance with an exemplary embodiment of the present invention.

FIG. 7 is a flow chart of a method 700 for determining whether to store prescription data for transmission to a switch from a pharmacy in accordance with an exemplary embodiment of the present invention. Method 700 begins at 702 where a scan is performed to determine whether a prescription data file exists. If it is determined at 704 that a file does not exist, the method proceeds to 714. Otherwise, the method proceeds to 706 where the prescription data file is processed. The method then proceeds to 708.

At 708, data is obtained from one or more secondary sources. In one exemplary embodiment, the secondary source can include a system for complying with the Health Insurance Portability and Accountability Act or other suitable systems that obtain data for patients in addition to data that is obtained as part of the claims process. The method then proceeds to 710.

AT 710, the prescription data is stored in an end-of-day file or other suitable data storage areas that are periodically checked for data. The method then proceeds to 712 where the data is transmitted to a data warehouse or other suitable locations where the data can be compiled for statistical analysis, storage. Or other suitable purposes. The method then proceeds to 714.

At 714, the prescription data is scanned for unprocessed cash transactions. In one exemplary embodiment, cash transactions can include transactions that are not submitted for claims processing, such as transactions for patients that do not have insurance or other suitable transactions. The method then proceeds to 716.

At 716, it is determined whether unprocessed prescription data exists. If it is determined that unprocessed prescription data does not exist, the method returns at 718. Otherwise, the method returns to 708.

Figure 8:
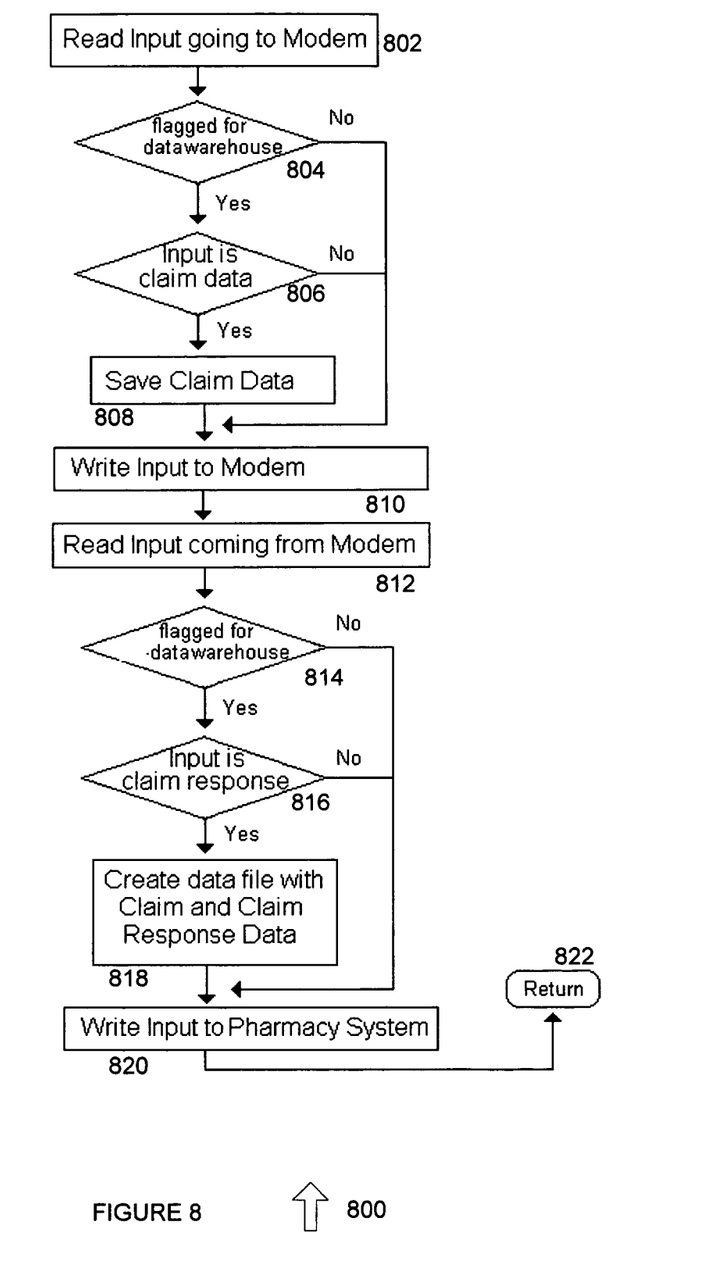
FIG. 8 is a flow chart of a method for monitoring prescription data in accordance with an exemplary embodiment of the present invention.

FIG. 8 is a flow chart of a method 800 for monitoring prescription data in accordance with an exemplary embodiment of the present invention. Method 800 begins at 802 where data that is transmitted to the modem is intercepted and read, such as through the use of a pseudo TTY, pseudo device, or other suitable processes. The method then proceeds to 804.

At 804, it is determined whether the data has been flagged for transmission to a data warehouse. If it is determined at 804 that the data has not been flagged, the method proceeds to 810. Otherwise, the method proceeds to 806 where it is determined whether the input is claim data. If it is determined at 806 that the input is not claim data, then the method proceeds to 810. Otherwise, the method proceeds to claim 808, where the claim data is saved in a suitable data storage location, such as a data warehouse, an end-of-day file, or other suitable locations. The method then proceeds to 810.

At 810, the input is written to a modem, such as by storing the input in a register dedicated to the modem or in other suitable manners. The method then proceeds to 812, where the input from the modem is read. At 814, it is determined whether the data has been flagged for transmission to a data warehouse. If it is determined at 814 that the data has not been flagged, the method proceeds to 820. Otherwise, the method proceeds to 816 where it is determined whether the input is claim response data. If it is determined at 806 that the input is not claim response data, then the method proceeds to 820. Otherwise, the method proceeds to claim 818, where the claim data is saved in a suitable data storage location, such as with the claim data, in a data warehouse, in an end-of-day file, or other suitable locations. The method then proceeds to 820.

At 820, the input is written to a pharmacy system, such as a system for generating accounting data, billing data, or other suitable data. The method then proceeds to 822, where the method returns.

Although exemplary embodiments of a system and method of the present invention have been described in detail herein, those skilled in the art will also recognize that various substitutions and modifications can be made to the systems and methods without departing from the scope and spirit of the appended claims.

What is claimed is:

1. A method for receiving prescription data from a pharmacy comprising:
in response to a prescription authorization system of a pharmacy computer at a first network location transmitting prescription data to a claims processor computer, the prescription authorization system transmitting the prescription data to a device emulation system which emulates a modem requiring a dial-up connection, which dial-up connection is currently unavailable to the pharmacy computer;
the pharmacy computer storing the prescription data in a local log file, wherein the local log file is local to the pharmacy computer; and
the pharmacy computer transmitting the prescription data from the device emulation system to a data warehouse computer at a second network location over an Internet connection, the transmitting occurring while a dial-up connection to the data warehouse computer is unavailable.

2. The method of claim 1 wherein transmitting the prescription data from the device emulation system to a data warehouse computer at a second network location over the Internet connection further comprises:
storing a marker in the log file if the Internet connection is unavailable; and
transmitting the contents of the log file starting at the marker and ending at the most recent entry when the Internet connection is available.

3. The method of claim 1 further comprising setting the prescription authorization system to transmit the prescription data to the device emulation system in response to transmitting the prescription data to the claims processor computer.

4. The method of claim 1 further comprising:
receiving the prescription data at the data warehouse computer;
storing the prescription data in a data warehouse log file associated with the pharmacy that transmitted the prescription data.

5. The method of claim 4 further comprising:
transmitting the local log file at an end of day;
comparing the local log file with the data warehouse log file to identify any entries in the local log file that are missing in the data warehouse log file; and
storing the missing entries and the data warehouse log file in the data warehouse computer.

6. The method of claim 1 further comprising:
receiving patient information relating to the prescription data from a secondary source; and
combining the patient information with the prescription data.

7. The method of claim 6 wherein the patient information is received from a Health Insurance Portability and Accountability Act information system.

8. The method of claim 1 wherein the device emulation system operates independently of a device driver.

9. The method of claim 1 wherein the transmitting prescription data comprises:
selecting one of two or more supported modem connections of the prescription authorization system, where the prescription authorization system can transmit the prescription data to each of the two or more supported modem connections in parallel; and
wherein the device emulation system is emulating a modem in one of the selected modem connections.

10. A system for receiving prescription data from a pharmacy comprising:
a pharmacy computer at a first network location, the pharmacy computer having:
device emulation system which emulates a modem requiring a dial-up connection, which dial-up connection is currently unavailable to the pharmacy computer;
a prescription authorization system configured to:
transmit prescription data to a claims processor computer; and
in response to transmitting prescription data to the claims processor computer, transmit prescription data to the device emulation system;
a local log file system configured to store the prescription data in a local log file after the device emulation system receives the prescription data, the local log file local to the pharmacy computer; and
an update system configured to transmit the prescription data from the device emulation system to a data warehouse computer at a second network location over an Internet connection, the transmitting occurring while a dial-up connection to the data warehouse computer is unavailable.

11. The system of claim 10 wherein the local log file system further comprises:
 a marker system generating tracking data for the prescription data if the Internet connection is unavailable; and
 a delayed update system receiving the tracking data and transmitting the contents of the log file based on the tracking data when the Internet connection is available.

12. The system of claim 10 wherein the prescription authorization system is configured to transmit the prescription data to the device emulation system in parallel with the provision of the prescription data to the claims processor computer.

13. The system of claim 10 further comprising the data warehouse computer, wherein the data warehouse computer is configured to:
 receive the prescription data over the Internet connection; and
 store the prescription data in a data warehouse log file associated with the pharmacy that transmitted the prescription data.

14. The system of claim 13 further comprising:
 an end of day system of the pharmacy computer configured to transmit the local log file at an end of day;
 a log file comparison system configured to compare the local log file with the data warehouse log file to identify any entries in the local log file that are missing in the data warehouse log file; and
 wherein the data warehouse computer is configured to store the missing entries in the data warehouse log file.

15. The system of claim 10 further comprising:
 a secondary source system configured to provide patient information relating to the prescription data; and
 a prescription data modification system configured to combine the patient information with the prescription data.

16. The system of claim 15 wherein the secondary source system is a Health Insurance Portability and Accountability Act information system.

17. The system of claim 10 wherein the device emulation system operates independently of a device driver.

18. The system of claim 10 wherein the prescription authorization system further comprises:
 two or more modem interface systems; and
 wherein the device emulation system emulates a modem receiving data from one of the modem interface systems.

* * * * *